United States Patent [19]

Neurath et al.

[11] 3,994,870

[45] Nov. 30, 1976

[54] PURIFICATION OF HEPATITIS B SURFACE ANTIGEN

[75] Inventors: A. Robert Neurath, New York, N.Y.; Alfred M. Prince, Stamford, Conn.; Arnold Lippin, Brooklyn, N.Y.

[73] Assignee: The Community Blood Council of Greater New York, New York, N.Y.

[22] Filed: Jan. 31, 1974

[21] Appl. No.: 438,269

[52] U.S. Cl. .............................. 260/112 R; 195/1.7; 210/DIG. 23; 260/112 B; 424/12; 424/86; 424/89
[51] Int. Cl.$^2$ ................. A61K 39/12; C07G 7/028; C12K 7/00
[58] Field of Search ....................... 195/1.9, 1.7, 1.8; 210/DIG. 23; 260/112 R, 112 B; 424/12, 86, 89

[56] References Cited
OTHER PUBLICATIONS

Stewart, et al., Chem. Abst. vol. 79 (1973), p. 15553n.
Neurath et al., Chem. Abst. vol. 79 (1973), p. 76761a.
Cawley, AJCP, vol. 57, Feb., 1972, p. 253.
Aspberg, Acta Chem. Scand., vol. 24, 1970, pp. 1839–1841.
Lloyd, Arch. Biochem. Biophys. vol. 137, 1970, p. 460.
Tripatzis, Nature, vol. 231, May 28, 1971, pp. 266–267.
Grabow, The J. of Inf. Dis., vol. 127, Feb. 1973, pp. 183–186.
Neurath, PSEBM, vol. 143, 1973, pp. 440–445.

*Primary Examiner*—Albert T. Meyers
*Assistant Examiner*—A. P. Fagelson
*Attorney, Agent, or Firm*—Burgess, Dinklage & Sprung; Burgess, Dinklage & Sprung

[57] ABSTRACT

After a polyethylene glycol purification procedure, virus particles, viral components and virus associated particles having concanavalin A binding sites are further purified by subjecting such particles or components to affinity chromatography utilizing insoluble concanavalin A as a chromatography adsorbent and an eluant capable of interacting with concanavalin A to thereby inhibit the binding of the virus particles or components to the insoluble concanavalin A. Specifically, the insoluble concanavalin A may be concanavalin A linked to agarose beads and the eluant may be methyl-$\alpha$-D-mannopyranoside. Specifically, these procedures may be utilized to purify hepatitis B antigen (HB Ag) particles.

5 Claims, No Drawings

PURIFICATION OF HEPATITIS B SURFACE ANTIGEN

ACKNOWLEDGEMENT OF H.E.W. SUPPORT:

The invention described herein was made in the course of work done under a contract with the National Institutes of Health, Department of Health, Education and Welfare.

BACKGROUND OF THE INVENTION

1. Field of the Invention

The present invention relates generally to the purification of virus particles, viral components and virus associated particles such as hepatitis B antigen (HB Ag) particles and particularly relates to the purification of the latter as a step in the production of commercial quantities of highly purified HB Ag which may be used in the commercial production of a vaccine against type B hepatitis infections.

2. Description of Prior Observations and Developments

In connection with medical research and particularly in connection with the evaluation and investigation of specific materials, it is necessary to isolate and purify the materials undergoing such evaluation and investigation so that the number of unknowns and variables are minimized, if not completely eliminated. Moreover, in the development and production of vaccines useful for immunization against specific diseases, it is desirable to isolate, insofar as is possible, specific virus particles themselves, viral components or virus associated particles having specific antigenic properties. Purified viruses and antigenic virus associated particles also have utility in determining the activity of immune globulins containing corresponding antibodies. Thus, methods for purifying specific viruses and related particles are highly useful in connection with both active and passive immunization and research activities associated therewith.

In particular, prior methods have been developed for purifying type B hepatitis antigen particles and preparing vaccines therefrom. Such methods are disclosed in U.S. Application of Prince, Ser. No. 301,347, filed Oct. 27, 1972, now abandoned entitled "HEPATITIS TYPE B VACCINE" and in U.S. Application of Vnek and Prince, Ser. No. 426,825, filed Dec. 20, 1973, now U.S. Pat. No. 3,951,937, entitled "LARGE SCALE PURIFICATION OF HEPATITIS TYPE B ANTIGEN," the disclosures of each of which are specifically incorporated herein by reference.

Further, prior methodology for passive immunization is disclosed in U.S. Application of Prince and Woods, Ser. No. 298,243, filed Oct. 17, 1972, entitled "HEPATITIS B IMMUNE GAMMA GLOBULIN." The disclosure of this application is also specifically incorporated herein by reference.

The foregoing applications specifically relate to an antigen detected during the incubation period and early clinical course of post-transfusion serum hepatitis as discussed by Prince, *Proc. Nat. Acad. Sci. U.S.A.* 60:814–821 (1968). This antigen appears to be identical to the so-called Australia antigen (See Prince, *Lancet* 2:462–463 (1968); Blumberg, Sutnick and London, *J. Am. Med, Assoc.* 207:1895–1896 (1969), and Wright, McCollum and Klatskin, *Lancet* 2:118–121 (1969)), and an exchange of reference reagents has established identity between this antigen and the "hepatitis antigen" of Gocke and Kavey, *Lancet* 1:1055–1059 (1969). The antigen has been described by Prince, Hargrove, Szmuness, Cherubin, Fontana and Jeffries, *N. Engl. J. Med.* 282:287–291 (1970) as being specific for the virus of serum hepatitis, a virus which appears to be a major cause of sporadic hepatitis in urban adults, regardless of the presence or absence of parenteral exposure to blood or blood products.

The antigen associated with such serum hepatitis infections has previously been called by a variety of names such as Australia antigen, SH antigen, Au/Sh antigen, HAA, etc., and each of these names has had its supporters. However, each also has inherent defects. Geographic names make life difficult for students and physicians and HAA ignores the evident specificity of this antigen for infections with type B hepatitis virus. The term SH, has the unfortunate connotation that this antigen is associated with a virus transmissible only by "serum" or blood products; however, many lines of evidence now indicate clearly that hepatitis B virus (serum hepatitis virus) is also "infectious." Thus, the continued use of the term "serum hepatitis" is likely to result in more confusion that clarification. For this reason a special subcommittee was appointed by the National Research Council of the U.S. National Academy of Sciences to attempt, among other things, to suggest a better terminology. The terminology chosen returns to the classical terms hepatitis type A virus and hepatitis type B virus, which were employed in the 1940's and 50's. The antigen therefore logically becomes hepatitis B antigen (HB Ag) and the antibody directed towards this antigen becomes hepatitis B antibody (HB Ab). Such terminology will be used herein.

In 1964 Blumberg, *Bull. N.Y. Acad. Med.* 40:377–386 (1964) described the discovery of what then appeared to be another human serum protein polymorphism. An antibody was detected in the serum of a multiply transfused hemophiliac which reacted in the Ouchterlony technique with an antigen which was not $\beta$-lipoprotein and which was found to be present in the sera of a proportion of certain foreign populations and in the sera of some patients with leukemia. The antigen was called the Australia antigen since it was initially detected in the serum of an Australian aborigine. Family studies appeared to support the hypothesis that this antigen was a genetically determined isoantigen. The Australia antigen was subsequently shown to be present in about 25% of institutionalized patients with Down's syndrome.

A chance observation by Blumberg provided grounds for a net interpretation of the prior findings discussed above. Serial blood samples were obtained from a child with Down's syndrome. Although the child did not initially have detectable antigen, a subsequent sample gave positive results. Clinical data revealed that at almost the same time the child developed hepatitis. It was then found that the antigen was present in 5 out of 48 sera from patients with viral hepatitis.

These data were compatible with at least three hypothesis: (1) that the antigen was a genetically determined serum isoantigen whose presence correlated with susceptibility to a variety of diseases or disease agents, e.g., leukemia, mongolism, hepatitis (2) that the antigen was a genetically determined isoantigen whose expression depended on the presence of a "derepressing" virus; and (3) that the antigen was specifically associated with a virus causing one or more of these conditions.

At first, the latter hypothesis was considered to be the least likely, since it was not anticipated that a viral antigen would circulate in healthy carriers in quantities sufficient for detection by an insensitive immunodiffusion assay. However, the results of a collaborative study by Prince and Blumberg of the physical characteristics of the antigen supported the third hypothesis since the antigen was found to be associated with a particle that sedimented at the rate of a small virus-like particle.

Specific association between Australia antigen and hepatitis was, however, not made until the composition of the agar employed for the immunodiffusion test had been changed. The precipitation lines were only then sufficiently clear to permit identity testing. The results obtained with the recently developed immunodiffusion system are described by Prince, *Proc. Nat. Acad. Sci.* 60:814–821 (1968).

Jokelainen, Krohn, Prince, and Finlayson, *J. Virol* 6:685–689 (1970) investigated the structural aspects of hepatitis B antigen-containing particles with an electron microscope and confirmed the existence of large spherical particles (ca. 43 nm) and smaller (ca. 20 nm) rod- and sphere-shaped particles. The larger particles seem to include outer and inner membranes and a core as seen by positive staining techniques. The outer membranes of the large particles appear to be similar to the 20 nm diameter spheres and rods known to possess the hepatitis B antigen. Each of the three kinds of particles appears to contain the hepatitis B antigen, because they are all clumped by hepatitis B antiserum.

Occasional large particles have projections with a structure identical to that of the rod forms, and constrictions along these in some instances give rise to an appearance suggesting a series of small spherical particles. These findings appear to agree with the findings of Dane, Cameron and Briggs, Lancet 1:695–698 (1970) that all of these forms are produced de novo and that the small spheres and rods may represent an excessive production of membrane material.

Studies with negative staining have confirmed the virus-like appearance of the large spherical particles. Positive-staining studies have indicated three further points: (i) the larger particles have a double membrane structure; (ii) the central core of the nucleoid-like component contains material which stains with uranyl acetate; and (iii) the small spheres and rods do not contain any core material. Although uranyl acetate cannot be considered a specific stain for nucleoprotein, it is recognized as being taken up preferentially by that material and this would be expected to occur within the core of a virus. Therefore, these findings support the hypothesis that, of the three hepatitis B antigen-containing particles described, the larger 40 to 45 nm particles are most probably the actual hepatitis B virus.

Krugman et al, *J. Am. Med. Assoc.* 217:41 (1971), have provided preliminary data suggesting that serum containing HB Ag which has been inactivated by boiling for one minute is noninfectious, immunogenic and protective when administered to a small group of volunteer children.

Prince, Szmuness, Hargrove, Jeffries, Cherubin and Kellner have presented a comprehensive report on the status of research activities directed to investigating the hepatitis B virus specific antigen in *Perspectives in Virology*, Vol. 7, Chap. 14, pp. 241–296 (Academic Press, Inc., 1971).

It has thus been shown that HB Ag is present in serum during the incubation period of classical post-transfusion serum hepatitis. Antibody to this antigen has been found in patients who have been multiply transfused, such as patients with hemophilia and Cooley's anemia. The antibody is usually not detected in sera from convalescent patients with typical cases of viral hepatitis. The hepatitis B antigen has been found to be identical with the previously described Australia antigen, and with the "hepatitis antigen" of Gocke. The antigen has been shown to be associated with virus-like particles 20 to 25 nanometers in diameter and has a density of approximately 1.17. Sera from patients with acute viral hepatitis have been tested for the presence of HB Ag to determine whether this would permit distinction between the two major types of viral hepatitis. None of 4 cases of short incubation MS-1 infection tested had detectable antigen; whereas the antigen was identified in all 8 cases of long incubation MS-2 infection tested. Correspondingly, only one out of 74 cases associated with four epidemics of infectious hepatitis, and none of 19 sporadic cases occurring in children under the age of 14 showed precense of detectable antigen; while 76 of 116 cases (66%) which occurred following exposure to contaminated needles and 25 of 43 post-transfusion cases (58%) were positive.

HB Ag has also been detected in 71 of 129 patients (55%) with viral hepatitis who gave no history of parenteral exposure.

These findings suggest that hepatitis B virus is the major cause of sporadic hepatitis in urban adults regardless of the presence or absence of parenteral exposure to blood or blood products.

HB Ag has been found to be 10 to 100 times more prevalent in tropical populations than in volunteer blood donors in New York City. These findings confirm previous results obtained by testing for the Australia antigen.

Although about 90 to 95% of patients with acute serum hepatitis in whom antigen is detected have detectable HB Ag in the blood only for short periods, some persons develop long lasting hepatitis B antigenemia. Long term persistence of antigen is also seen in clinically well individuals in all populations which have been examined.

Two to three percent of drug users without evidence of acute hepatitis have detectable quantities of HB Ag. By comparison, the antigen can be detected in only 0.1 percent of the volunteer blood donors in New York City. Paid blood donors, who have been reported to be at least 10 times as likely as volunteer donors to transmit hepatitis, have also been found to be 12.5 times as likely as the volunteer donors to show the presence of HB Ag in their blood.

Moreover, HB Ag has been found in the serum of 8 of 138 chimpanzees tested. The antigen has persisted for at least 5 years in 3 of these animals. This antigen has not been found in the serum of 99 baboons and 11 gibbons. Antigenemic chimpanzees were found to have histologic evidence of chronic persisting hepatitis. HB Ag was found in 6 of 138 chimpanzees and was transient in 3 of these animals. The chimpanzee antigen carrier provides a useful animal model for study of the hepatitis B virus carrier state and approaches to its therapy.

It appears likely that chronic HB Ag carriers are also hepatitis B virus carriers since blood containing the antigen has given rise to hepatitis in at least 5 out of 8 recipients in one study and 9 out of 12 in a second.

The presence of HB Ag and HB Ab may be quantitatively detected by agar gel diffusion using the methodology described by Prince, *Proc. Nat'l. Acad. Sci. U.S.A.* 60:814–821 (1968), by IEOP as described by Prince and Burke, *Science* 169:593–595 (1970), by passive hemagglutination (HA) and hemagglutination inhibition (HAI) as described by Vyas and Shulman, *Science* 170:332–333 (1970) and more recently by the direct radio-immuno assay (RIA) of Ling and Overby utilizing Ausria kits supplied by Abbott Laboratories.

It has been estimated that the plasma of hepatitis B virus carriers contains up to 1.0 mg of antigen associated protein per ml of plasma. Carrier plasma may therefore serve as a useful source of antigen for production of vaccines.

Prince, in his U.S. patent application Ser. No. 301,347, filed Oct. 27, 1972, referred to above, the entirety of which is specifically incorporated herein by reference, discloses a vaccine against type B hepatitis infections, a method for production of such a vaccine and a vaccination process which makes use of the vaccine. Specifically, Prince's vaccine includes HG Ag particles having a diameter of from about 16 to about 30 nanometers in a physiologically acceptable carrier. The vaccine is substantially free of the larger, probably infectious HB Ag particles having a diameter of about 40 to 45 nm.

Prince, in his application, makes use of a purification process involving Freon extraction and methanol precipitation followed by zonal ultracentrifugation. The zonal ultracentrifugation procedures disclosed by Bond and Hall, *J. Infect. Dis.* 125:263–268 (1972) are disclosed by Prince as being appropriate for separation and purification of HB Ag into its morphologic forms; however, the procedures disclosed are hazardous and therefore special safety facilities are required. Moreover, these zonal ultracentrifugation procedures are extremely costly and the large total quantity of material which is fed to the ultracentrifuge in the method of application Ser. No. 301,347 per unit of product results in an extremely high cost of production for the purified antigen. Accordingly, less expensive methods for production of HB Ag are desirable so that the vaccines produced therefrom will be generally available to the public at a price which can be borne without substantial hardship on the part of either the individual or the government. Further, it has been found that the larger 40 to 45 nm particles purified by rate zonal sedimentation are somewhat lacking in stability and therefore it is believed that milder purification techniques might be desirable for some purposes.

Polson, in U.S. Letters Pat. No. 3,415,804, discloses methods for fractionating mixtures of proteinacious substances using polyethylene glycol (PEG) as a precipitating agent to produce a liquid phase containing one fraction in soluble form and a solid phase containing a second fraction. In the Polson method, which involves the use of a pH of 7.0, a temperature of 21° C and protein concentrations less than 0.4 grams per 100 ml, a PEG concentration greater than 12% is required to precipitate $\alpha$-globulins and albumin. Polson suggests that the higher the protein concentration, the greater the overlap between fractions. Moreover, although HB Ag is normally considered to be associated with the $\alpha$-globulin fractions, Polson does not disclose any method suitable for separating HB Ag from any of the fractions obtained from plasma. Further, very large concentrations of PEG are required by Polson to effect his desired fractionations.

De Rizzo, Pandey, Wallis and Melnik, *Inf. and Imm.* 6:335–338 (1972) have disclosed a two step method for concentrating and purifying HB Ag utilizing PEG and polyelectrolyte 60 (a cross-linked copolymer of isobutylene maleic anhydride). In the first step, plasma having a protein concentration of 79.9 mg/ml is subjected to PEG precipitation at a pH of 4.6 and a temperature of 25° C, utilizing a PEG concentration of 8%. It is indicated that the precipitate contains 100% of the original HB Ag and only 12.5% of the original proteins. The proteins in the precipitate comprise 2 mg of albumin per ml, 3 mg of $\alpha_2$-globulin per ml and 5 mg of gamma-globulin per ml. It was reported that all of the $\alpha_1$, $\beta_1$ and $\beta_2$ globulins remained in the liquid phase. The precipitate thus obtained, by precipitation with PEG, was then subjected to concentration and purification of the HB Ag therein utilizing polyelectrolyte 60. Eight-fold purification of the HB Ag in the PEG precipitation step was reported by De Rizzo et al; however, attempts to utilize the De Rizzo et al method by associates of the present applicants have indicated that the procedure provides only a two-fold purification. Furthermore, it has been found that the De Rizzo et al method is not reproducible as described.

Blumberg and Millman, in U.S. Letters Pat. No. 3,636,191, have disclosed methods for producing a vaccine against viral hepatitis wherein plasma containing the antigen is subjected to ultracentrifugation, enzyme digestion, column gel filtration, differential density centrifugation in a solution of sucrose, dialysis, differential density centrifugation in a solution of cesium chloride and dialysis. The disclosed method is very expensive and is not suitable for the large scale purification of HB Ag. Further, it has been suggested that the antigen may be altered by proteolytic digestion. Moreover, the procedure disclosed does not appear to separate the larger HB Ag associated particles which occur in donor carrier plasma.

Vnek and Prince, in their U.S. Patent Application Ser. No. 426,825, filed Dec. 20, 1973 now U.S. Pat. No. 3,951,937, and referred to above, the entirety of which is specifically incorporated herein by reference, disclose a completely reproducible and highly efficient method for the large scale purification of HB Ag for use in the commercial production of a vaccine against type B hepatitis infections. The method of Vnek and Prince utilizes, as an initial feed, fluid blood material containing HB Ag. In accordance with their disclosure, the pH of the fluid blood material is maintained at approximately 4.4 to 4.7 while approximately 4.0 to 4.5 weight percent PEG, based on the total weight of the resultant admixture, is admixed therewith to produce a precipitate containing the antigen. The precipitate is separately recovered and sufficient water is added thereto present an intermediate fluid material having an The pH substantially the same as the original blood material. the pdH of the intermediate fluid material is caused to be within the range of approximately 4.9 to 5.1 to thereby produce a precipitate containing proteinaceous material and polyethylene glycol and a fluid phase containing the antigen. The fluid phase is separately recovered and the pH thereof is adjusted to within the range of 4.4 to 4.7. The fluid phase, while its pH is maintained within the foregoing range, is admixed with approximately 4.0 to 4.5 weight percent PEG based on the total weight of the admixture to produce a precipitate containing purified HB Ag which precipitate is separately recovered.

More specifically, in accordance with Vnek and Prince, it has been found that precipitation procedures utilizing PEG at a pH of 4.4 to 4.7 to produce a precipitate containing purified HB Ag may be carried out much more efficiently at a temperature in the range of approximately 0° to 8° C.

The Vnek and Prince precipitate containing the purified HB Ag may be further subjected to purification by adsorption of protein contaminants to hydroxy apatite followed by isopycnic banding and then zonal ultracentrifugation for separating the morphological forms of the antigen. While the latter procedures are quite expensive, as outlined above, the double polyethyleneglycol precipitation procedure summarized above provides a highly purified material whereby the total volume fed to the ultracentrifuge per unit of recovered relatively non-infectious 20 nanometer spherical particles is substantially less than in the method described in the Prince application, Ser. No. 301,347, and as a result, the cost of production is substantially reduced.

As a further aspect of the Vnek and Prince methods, they found that purified HB Ag can be separated into three different populations, each rich in a different one of the three morphological forms of HB Ag particles by a process which comprises applying a quantity of an aqueous fluid containing a substantial concentration of purified HB Ag to a hydroxy apatite chromatography column, thereafter eluting the column with a three step graduated eluant and then separately collecting at least three distinct portions of the eluate from the column. Accordingly, the necessity for extensive zonal ultracentrifugation is substantially reduced.

Thus, new specific and/or improved methods for purifying viruses or antigenic virus associated particles for use in preparing vaccines, for use in preparing passive immunization agents, for use in evaluating immune globulins or for use in preparing diagnostic reagents are continually sought by those skilled in the art to which the present invention pertains. Cawley, for example, in his communication reported in *Am. J. Clin. Pathol.* 57:253 (1972), disclosed that a material designated concanavalin A (Con A), which is soluble in aqueous solution, is capable of binding HB Ag to form a precipitate which can be separated from the serum. While Cawley suggests the use of methyl mannopyranoside to solubilize the complex of Con A and HB Ag, he does not disclose an effective method for the quantitative separation of HB Ag from Con A, a step which is obligatory in the purification of HB Ag.

SUMMARY OF THE INVENTION

The present invention provides a new and highly useful method for purifying viruses, viral components and virus associated particles having Con A binding sites. More specifically, the invention provides a particularly useful method for purifying HB Ag particles. The method comprises subjecting the material to be purified to affinity chromatography utilizing insoluble Con A as a chromatography adsorbent. Preferably the insoluble Con A is produced by linking soluble Con A with an insolubilizing agent such as agarose beads.

In accordance with conventional affinity chromatography procedures, a fluid material containing the materials, components or particles to be purified as applied to aa chromatography column containing the insoluble Con A and thereafter the column is eluted. Generally the eluants used in connection with the present invention are capable of interacting with Con A to thereby inhibit the binding of the components or particles to the insoluble Con A. Some saccharides are particularly useful eluants for affinity chromatography using insoluble Con A and methyl-α-D-mannopyranoside is the preferred eluant for use with Con A linked to agarose beads.

DESCRIPTION OF THE PREFERRED EMBODIMENTS

In accordance with the present invention, it has been found that virus particles, viral components and virus associated particles having Con A binding sites, such as exposed saccharides with terminal α-D-mannopyranosyl, α-D-glucopyranosyl or β-D-fructofuranosyl residues, may be purified by affinity chromatography utilizing insoluble Con A as a chromatography adsorbent. These procedures are discussed by the present applicants in an article entitled "Affinity Chromatography of Hepatitis B Antigen on Concanavalin A linked to Sepharose", *J. Gen. Virol.* 19:391–395 (1973), the entirety of which is specifically incorporated herein by reference. More specifically, such procedures may be utilized to purify HB AG particles including any or all of the distinct morphological forms of the latter.

Concanavalin A is a lectin isolated from jack beans which binds specifically to saccharides having terminal α-D-mannopyranosyl, α-D-glucopyranosyl, or β-D-fructofuranosyl residues as disclosed by Goldstein et al, *Biochem. Biophys. Acta.* 97:68–76 (1965); Boldstein et al, *Biochem.* 4:876–883 (1965) and Goldstein et al, *Arch. Biochem. Biophys.* 111:407–414 (1965). Moreover, it has been previously shown that glycoproteins present in human serum (See Leon, *Science* 158:1325–1326 (1967) and Morse, *Immunology* 14: 713–724 (1968)) or representing structural components of membranes of mammalian cells (See Ibar et al, *Proc. Nat. Acad. Sci. U.S.A.* 63:1418–1425 (1969))or of enveloped viruses (see Oram et al, *Nature New Biology* 233:50–51 (1971); Becht et al, *J. Gen. Virol.* 14: 1–8 (1972); Calafat et al. *J. Gen Virol.* 14: 103–106 (1972); and Klenk et al, *Virology* 47:579–591 (1972)) react with Con A. Further, as discussed above, Cawley observed that Con A partially precipitates HB Ag particles; however, no procedure was presented by Cawlay for recovering the antigen particles from the Con A. In accordance with the present invention, insoluble Con A is utilized as an affinity chromatography adsorbent for purifying virus particles, viral components and virus associated particles such as all forms of HB Ag particles. The purified material is separated from the insoluble Con A with an eluant capable of interacting with Con A to thereby inhibit the binding of the particles or components being purified to the insoluble Con A.

It is believed that any form of insoluble Con A should be operable in connection with the present invention. Insoluble Con A is produced by linking soluble Con A with an insolubilizing agent. Two specific forms of insoluble Con A and methods for their preparation are disclosed by Lloyd, *Arch. Biochem. Biophys.* 137:460–468 (1970), the entirety of which disclosure is specifically incorporated herein by reference. The insoluble Con A which is particularly preferred in connection with the present invention consists of Con A coupled with Sepharose (Con A-Sepharose) which is fully described, along with its method of production, by Porath et al, *Nature London* 215:1491 (1967) which disclosure is also specifically incorporated by reference. Specific reference is also made to Aspberg et al, *Acta. Chem. Scand.* 24:1839–1841 (1970), Axen et al, *Nature* 214:1302 ff. (1967) and Porath et al, *Nature* 215:5109 ff. (1967), each of which discuss insoluble Con A, its properties and characteristics. Specifically, Sepharose is a commercial name utilized to designate beads of agarose gel and Sepharose 2B specifically refers to beads of activated 2% agarose gel and in this connection it is pointed out that one known activating agent for agarose gel beads comprises cyanogen bromide. it is believed, in accordance with the broader aspects of the invention, however, that insoluble Con A might also be produced merely by linking or coupling soluble Con A with glass beads.

The insoluble Con A is used as a chromatography adsorbent to purify virus particles, viral components or virus associated particles having Con A binding sites. Affinity chromatography procedures are utilized wherein a fluid material which contains the components or particles to be purified is applied to a chromatography column which contains the insoluble Con A adsorbent. The purified particles are recovered by eluting the column with an eluant capable of interacting or reacting with insoluble Con A to inhibit the binding of the particles or components to the insoluble Con A. Certain polysaccharides possess such a capability and a preferred eluant is methyl-$\alpha$-D-mannopyranoside. A multitude of additional eluants operable to inhibit Con A in accordance with the present invention are disclosed by Goldstein et al, *Biochem.* 4:876–883 (1965). Also, it has been found that ethylenediaminetetraacetate (EDTA) is particularly useful as an eluant for eluting influenza virus from insoluble Con A.

The following specific examples illustrate methods for purifying virus associated particles by affinity chromatography utilizing insoluble Con A as a chromatography adsorbent.

EXAMPLE I 1 ml of HB Ag-positive serum was applied to the top of a 17 × 1 cm column containing Con A-Sepharose which has been prewashed with an aqueous solution containing 0.14 mols/liter of NaCl, 0.01 mols/liter of tris(hydroxymethyl)aminomethane (Tris), 0.001 mols/liter of $CaCl_2$ and 0.001 mols/liter of $MnCl_2$ and having a pH of 7.2. (This solution will be referred to hereinafter as TCaMn). After application of the HB Ag-positive serum to the prewashed column, the latter was washed with 20 ml of TCaMn. Then an aqueous eluant solution containing 5.0% (w/v) methyl-$\alpha$-D-mannopyranoside (MMP), 0.14 mols/liter NaCl and 0.01 mols/liter Tris was applied to the column to elute the HB Ag particles. Fractions of 1.2 ml each were collected. The results indicate that approsimately 82% of the serum proteins were removed from the antigen by affinity chromatography. Further experiments utilizing essentially the same procedures showed that the maximal volume of serum which could be chromatographed under conditions allowing complete retention of HB Ag particles corresponded to approximately 24% of the volume of the Con A-Sepharose adsorbent in the column. The adsorbent could be reused and no losses activity were detected within three months.

HB Ag, partially purified by the procedures described above, was further purified by molecular exclusion chomatography on a 56 × 0.9 cm column of controlled-pore glass beads (498 A pore size, 120 to 200 mesh; produced by Electro Nucleonics, Incorporated, Fairfield, New Jersey). The beads were coated with PEG 20,000 in accordance with the methodology described by Hawk et al, *Prep. Biochem.* 2:193–202 (1972). After coating with PEG, the glass beads were washed with 50 ml of an aqueous solution containing 0.5% (w/v) bovine hemoglobin, 0.14 mols/liter NaCl, 0.05 mols/liter Tris and 0.005 mols/liter ethylenediaminetetraacetate (EDTA) and having a pH of 7.5. After the PEG coated glass beads were washed with the solution containing bovine hemoglobin, the washing thereof was continued with an identical solution (0.14 M-NaCl, 0.05 M-Tris and 0.005 M-EDTA) but without the bovine hemoglobin until the concentration of hemoglobin in the effluent wash solution decreased to 0.005% as monitored spectrophotometrically. Thereafter, the column was washed with 50 ml of an aqueous solution containing 0.5% PEG 300,000 followed by 50 ml of an elution buffer comprising an aqueous solution containing 0.005% hemoglobin, 0.02% PEG 20,000, 0.14 mols/liter NaCl, 0.05 mols/liter Tris and 0.005 mols/liter EDTA. Fractions corresponding to the void volume of the column and containing HB Ag, were pooled, concentrated to 1 ml by ultrafiltration, layered on top of 1 ml of an aqueous solution containing25% (w/v) sucrose, 0.14 mols/liter NaCl and 0.01 mols/liter Tris, and centrifuged for 3 hours at 50,000 rpm in a Spinco rotor SW 65 centrifuge. The pellet was resuspended in 0.3 ml of an aqueous buffer solution containing 0.025 mols/liter of a phosphate buffer and having a pH of 7.2. The pellet was then negatively stained with a 1% phosphotungstate solution and was examined by electron microscopy. (The specimens were deposited on carbon-coated grids and a JEM-100B electron microscope was used. Pictures were taken at a magnification of 40,000x at 60kV.) Spherical particles of approximately 40 and 22 nm diameter and rods having a width of 22 nm were observed. Accordingly it was shown by this experiment that all three morphological forms of HB Ag which share common surface antigens (See Dane et al, *Lancet* 1:695–698 (1970); Gust et al, *Lancet* 1:953 (1970); Jokelainen et al, *J. Virol.* 6:685–689 (1970); and Cossart et al, *Microbios* 3, 5–14 (1971)) have Con A binding sites exposed on their surfaces that is, they all appear to have exposed saccharides with terminal $\alpha$-D-mannopyranosyl, $\alpha$-D-glycopyranosyl or $\beta$-D-fructofuranosyl residues.

As illustrated in the foregoing Example, the methods of the present invention contribute significantly to the purification and separation of the different morphological forms of HB Ag particles and these particles have preserved biological activity.

EXAMPLE II

4 ½ ml of an aqueous solution containing 30% (w/v) PEG 6,000 were added to 20 ml of an HB Ag-containing serum. The mixture was maintained at a temperature of 4° C overnight and the precipitate was further sedimented by centrifugation at 4500g for 20 minutes. The supernatant fluids from the precipitation step and from the centrifugation step were pooled and were subjected to affinity chromatography utilizing a 33 × 1 cm column of Con A-Sepharose. Similarly to the procedure set forth in Example I, the column was prewashed with TCaMn. The supernatant fluid from the PEG precipitation step had a volume of approximately 24 ml and contained PEG soluble HB Ag particles and prior to the affinity chromtography step, a sufficient amount of $CaCl_2$ and $MnCl_2$ were added to the supernatant fluid so that the latter was 0.001 M with respect to each of these materials. The supernatant fluid containing the PEG soluble HB Ag particles was then applied to the prewashed column and thereafter the latter was washed with 37 ml of TCaMn. Thereafter, an aqueous eluant solution containing 5% (w/v) MMP, 0.14 mols/liter NaCl and 0.01 mols/liter of Tris was applied to the column to elute the HB Ag. Fractions of 2 ml each were collected and assayed for HB Ag by immunoelectroosmophoresis utilizing the procedures described by Prince et al, Science 169:539 (1970). Fractions 40 through 56 obtained through the use of the foregoing affinity chromatography procedure were found to contain 91% of the PEG soluble HB Ag particles and only 6.4% of the total protein originally present in the serum. This compares with the fact that the supernatant fluid from the PEG precipitation step contained approximately 78% of the total protein originally present in the serum. Accordingly, the PEG soluble HG Ag particles were purified extensively through the use of affinity chromatography utilizing Con A-Sepharose as a chromatography adsorbent.

In further evaluation of the results obtained in Example II, it is to be recognized that in addition to the 42 nm particles and the tubular forms of HB Ag, immunoglobulin M, $\alpha_2$-lipoproteins and $\beta_2$-lipoproteins are also precipitated by PEG. In view of the fact that $\alpha_2$-lipoproteins and immunoglobulin M are each capable of interacting with Con A (See Leon, Science 158:1325 (1967)), the removal of these components by PEG precipitation is extremely advantageous in the further purification of the smaller, spherical, PEG-soluble HB Ag particles by affinity chromatography and in fact it was found that the initial PEG precipitation step provided a two to three fold increase in the apparent capacity of Con A-Sepharose columns to combine HB Ag.

In addition to the foregoing it is recognized and is considered to be within the broad concepts of the present invention that any viral component having Con A binding sites may be purified by subjecting such viral components to affinity chromatography utilizing insoluble Con A as the chromatography adsorbent. Viruses, viral components and virus associated materials which are known to have Con A binding sites include, inter alia, in addition to all of the morphological forms of HB Ag: carcinoembryonic antigens; oncornaviruses such as murine leukemia virus and Friend virus; herpes simplex virus glycoproteins; influenza viruses; and other enveloped viruses. Moreover, it would be a simple matter for one of ordinary skill in this art to determine, by precipitation with Con A, which viruses, viral components and virus associated particles have Con A binding sites whereby the same may be purified by being subjected to affinity charomatography utilizing insoluble Con A as the chromatography adsorbent.

EXAMPLE III

In accordance with this Example, HB Ag is first purified utilizing the two-step PEG procedures described by Vnek and Prince in their application Ser. No. 426,825, filed Dec. 20, 1973, (U.S. Pat. 3,951,937) at pages 18 through 23. A product having a volume of 100 ml, having an HB Ag titer of 512 – 1024 and containing 3.6% of the total original protein in the plasma was thus produced. This product was subjected to affinity chromatography utilizing Con A-Sepharose as the adsorbent and the same procedures as described above in connection with Examples I and II. It was found that the apparent capacity of the Con A-Sepharose column to bind PEG soluble HB Ag particles was increased even more than three-fold by the further removal, by the two step PEG precipitation procedure of Vnek and Prince, of proteins which would othrwise interfere with affinity chromatography utilizing insoluble Con A-Sepharose as the adsorbent.

Accordingly, affinity chromatography utilizing insoluble Con A as a chromatography absorbent is highly useful in connection with processes for the large scale purification of HB Ag wherein PEG precipitation procedures are utilized. Moreover, it is specifically contemplated in connection with the present invention that affinity chromatography utilizing insoluble Con A as a chromatography adsorbent could be utilized in connection with the further purification of HB Ag particles and in particular to relatively non-infectious smaller diameter spherical HB Ag particles, which have been pre-purified by any method or means, such as, for example, by hydroxy apatite adsorption. Also it is within the specific contemplation of the present invention that affinity chromatography utilizing insoluble Con A as a chromatography adsorbent is useful in connection with the purification of any other virus particles, viral components and/or virus associated particles having Con A binding sites such as exposed saccharides with terminal $\alpha$-D-mannopyranosyl, $\alpha$-D-glucopyranosyl or $\beta$-D-fructofuranosyl residues.

We claim:

1. A process for separating hepatitis B surface antigen from other proteins in a proteinaceous fluid blood material which comprises adjusting the pH of said fluid blood material to about 4.4 to 4.7 and adding thereto 4.0 to 4.5 weight percent polyethylene glycol based upon the total weight of the resultant mixture thereby forming a precipitate; separating the precipitate and washing the same with water to prepare an intermediate fluid material containing hepatitis B surface antigen; adjusting the pH of the intermediate fluid material to within the range of 4.9 to 5.1 to thereby produce a precipitate containing proteinaceous material and polyethylene glycol and a fluid phase containing hepatitis B surface antigen, separating the fluid phase and adjusting the pH thereof to be within the range of 4.4 to 4.7 and adding thereto 4.0 to 4.5 weight percent polyethylene glycol based on the total weight of the admixture to produce a precipitate containing hepatitis B surface antigen, admixing said hepatitis B surface antigen so obtained with water to form a second fluid material, passing said second fluid material over insoluble concauavalin A as an affinity chromatography adsorbent, withdrawing protein free of concanavalin A binding site leaving thereon hepatitis B surface antigen bound to said insoluble concanavalin A and thereafter passing an eluent through said concanavalin A to thereby remove from said concanavalin hepatitis B surface antigen.

2. The method of claim 1 wherein said eluant is a saccharide.

3. The method of claim 2 whrein said saccharide is methyl-$\alpha$-D-mannopyranoside.

4. The method of claim 1 wherein said eluant is an exposed saccharide having terminal $\alpha$-D-mannopyranosyl, $\alpha$-D-glucopyranosyl or $\beta$-D-fructofuranosyl residue.

5. The method of claim 1 wherein said eluant is ethylenediaminetetraacetate.

* * * * *

UNITED STATES PATENT AND TRADEMARK OFFICE
CERTIFICATE OF CORRECTION

PATENT NO. : 3,994,870
DATED : NOVEMBER 30, 1976
INVENTOR(S) : A. ROBERT NEURATH, ALFRED M. PRINCE, ARNOLD LIPPIN

It is certified that error appears in the above-identified patent and that said Letters Patent are hereby corrected as shown below:

Column 2, line 51, "net" should read -- new --.
Column 6, lines 57-58, delete "The pH" and substitute
   therefor -- antigen concentration --;
        line 59, "the pdH" should read -- The pH --.
Column 8, line 31, "Boldstein" should read -- Goldstein --;
        line 38, "Ibar" should read -- Inbar --.
Column 12, line 60, "whrein" should read -- wherein --.

Signed and Sealed this

First Day of March 1977

[SEAL]

Attest:

RUTH C. MASON
Attesting Officer

C. MARSHALL DANN
Commissioner of Patents and Trademarks